(12) United States Patent
Rottmann et al.

(10) Patent No.: US 11,109,788 B2
(45) Date of Patent: Sep. 7, 2021

(54) CATHETER WITH FIBONACCI DISTRIBUTED ELECTRODES

(71) Applicants: BIOSENSE WEBSTER (ISRAEL) LTD., Yokneam (IL); Karlsruhe Institute of Technology, Karlsruhe (DE)

(72) Inventors: Markus Rottmann, Walzbachtal (DE); Olaf Dössel, Bruchsal (DE); Meir Bar-Tal, Haifa (IL); Yaniv Ben Zrihem, Binyamina (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 867 days.

(21) Appl. No.: 15/651,888

(22) Filed: Jul. 17, 2017

(65) Prior Publication Data

US 2019/0015007 A1    Jan. 17, 2019

(51) Int. Cl.
*A61B 5/042* (2006.01)
*A61B 5/287* (2021.01)
*A61B 5/00* (2006.01)
*A61M 25/00* (2006.01)

(52) U.S. Cl.
CPC ............ *A61B 5/287* (2021.01); *A61B 5/6858* (2013.01); *A61B 5/6859* (2013.01); *A61M 25/0074* (2013.01); *A61B 5/6853* (2013.01); *A61B 2562/0209* (2013.01); *A61B 2562/046* (2013.01)

(58) Field of Classification Search
CPC ... A61B 5/0422; A61B 5/6858; A61B 5/6859; A61B 5/6853; A61B 2562/0209; A61B 2562/046; A61M 25/0074
See application file for complete search history.

(56) References Cited

U.S. PATENT DOCUMENTS

| | | | |
|---|---|---|---|
| 5,443,470 A | 8/1995 | Stern et al. |
| 5,546,951 A | 8/1996 | Ben-Haim |
| 5,738,096 A | 8/1998 | Ben-Haim |
| 6,064,905 A | 5/2000 | Webster, Jr. et al. |
| 6,226,542 B1 | 5/2001 | Reisfeld |
| 6,301,496 B1 | 10/2001 | Reisfeld |

(Continued)

FOREIGN PATENT DOCUMENTS

| | | |
|---|---|---|
| EP | 1 332 724 A1 | 8/2003 |
| WO | WO 96/05768 A1 | 2/1996 |

OTHER PUBLICATIONS

Pending U.S. Appl. No. 15/086,220, filed Mar. 31, 2016.
European Search Report dated Dec. 13, 2018, Application No. EP 18 18 3654.

*Primary Examiner* — Eun Hwa Kim
*Assistant Examiner* — Adam Z Minchella

(57) ABSTRACT

A catheter has a mapping assembly having a plurality of splines mounted at its distal portion. The splines each have a proximal end disposed at the distal portion of the catheter body and a distal end and configured as a Fibonacci spiral arm that diverges outwardly from the proximal end. The splines have a support arm with shape memory, a non-conductive covering in surrounding relation to the support arm, at least one location sensor mounted at or near the distal end, a plurality of electrodes mounted in surrounding relation to the non-conductive covering, and a plurality of electrode lead wires extending within the non-conductive covering. Each electrode lead wire is attached to a corresponding one of the electrodes.

24 Claims, 9 Drawing Sheets

(56) References Cited

U.S. PATENT DOCUMENTS

| | | | |
|---|---|---|---|
| 6,690,963 B2 | 2/2004 | Ben-Haim | |
| 6,814,733 B2 | 11/2004 | Schwartz et al. | |
| 6,892,091 B1 | 5/2005 | Ben-Haim et al. | |
| 6,997,924 B2 | 2/2006 | Schwartz et al. | |
| 7,156,816 B2 | 1/2007 | Schwartz et al. | |
| 7,536,218 B2 | 5/2009 | Govari et al. | |
| 7,756,576 B2 | 7/2010 | Levin | |
| 8,478,383 B2 | 7/2013 | Bar-Tal et al. | |
| 9,352,134 B2 | 5/2016 | Levin et al. | |
| 2006/0276703 A1 | 12/2006 | Fuimaono et al. | |
| 2011/0160574 A1 | 6/2011 | Harlev et al. | |
| 2012/0016342 A1* | 1/2012 | Brecker | A61M 25/09025 604/528 |
| 2013/0261702 A1 | 10/2013 | Garfield et al. | |
| 2013/0345583 A1* | 12/2013 | Thakur | A61B 5/316 600/523 |
| 2014/0257069 A1* | 9/2014 | Eliason | A61B 5/6858 600/373 |
| 2015/0208937 A1* | 7/2015 | Bullinga | A61B 5/287 600/424 |
| 2015/0327921 A1 | 11/2015 | Govari et al. | |
| 2016/0175041 A1 | 6/2016 | Govari et al. | |
| 2016/0324571 A1 | 11/2016 | Beeckler et al. | |
| 2018/0192959 A1* | 7/2018 | Mou | A61B 18/1492 |

* cited by examiner

Spacing

| | st-1 | 1-2 | 2-3 | 3-4 | 4-5 |
|---|---|---|---|---|---|
| Spline 1 | 1 | 8.2415 | 9.2264 | 10.8769 | 12.9437 |
| Spline 2 | 2 | 8.3222 | 9.4031 | 11.1159 | 13.2198 |
| Spline 3 | 3 | 8.4167 | 9.5894 | 11.3606 | 13.4994 |
| Spline 4 | 4 | 8.5244 | 9.7847 | 11.6108 | 13.7822 |
| Spline 5 | 5 | 8.6448 | 9.9884 | 11.8661 | 14.0681 |
| Spline 6 | 6 | 8.7776 | 10.2002 | 12.1261 | 14.3568 |
| Spline 7 | 7 | 8.9220 | 10.4194 | 12.3906 | 14.6482 |
| Spline 8 | 8 | 9.0777 | 10.6456 | 12.6593 | 14.9422 |

54

Spline Equation

$$p(x) = p_1 x^n + p_2 x^{n-1} + \ldots + p_n x + p_{n+1}$$

56

| p3 | p2 | p1 | p0 |
|---|---|---|---|
| 0.0028 | 0.0475 | -0.0260 | 1.1875 |
| 0.0013 | -0.0163 | -0.8074 | -2.1082 |
| 0.0018 | -0.0271 | -1.2474 | 5.7880 |
| 0.0005 | -0.0096 | -0.3305 | -1.8406 |
| 0.0003 | 0.0000 | -0.0560 | -1.4199 |
| 0.0002 | 0.0042 | -0.1191 | -0.6470 |
| 0.0004 | 0.0050 | -0.3516 | -3.7303 |
| -0.0000 | -0.0023 | -0.0358 | 1.0920 |

CATHETER WITH FIBONACCI DISTRIBUTED ELECTRODES

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

This invention relates to detecting, measuring or recording bioelectric signals of the body. More particularly, this invention relates to analysis of electrical signals of the heart for diagnostic purposes.

2. Description of the Related Art

Cardiac arrhythmias such as atrial fibrillation are an important cause of morbidity and death. Commonly assigned U.S. Pat. Nos. 5,546,951, and 6,690,963, both issued to Ben Haim, and PCT application WO 96/05768, all of which are incorporated herein by reference, disclose methods for sensing an electrical property of heart tissue, for example, local activation time, as a function of the precise location within the heart. Data are acquired with one or more catheters having electrical and location sensors in their distal tips, which are advanced into the heart. Methods of creating a map of the electrical activity of the heart based on these data are disclosed in commonly assigned U.S. Pat. Nos. 6,226,542, and 6,301,496, both issued to Reisfeld, which are incorporated herein by reference.

As indicated in these patents, location and electrical activity are typically initially measured on about 10 to about 20 points on the interior surface of the heart. These data points are then generally sufficient to generate a preliminary reconstruction or map of the cardiac surface. The preliminary map is often combined with data taken at additional points in order to generate a more comprehensive map of the heart's electrical activity. Indeed, in clinical settings, it is not uncommon to accumulate data at 100 or more sites to generate a detailed, comprehensive map of heart chamber electrical activity. The generated detailed map may then serve as the basis for deciding on a therapeutic course of action, for example, tissue ablation, to alter the propagation of the heart's electrical activity and to restore normal heart rhythm.

Activation time differs from point to point in the endocardium due to the time required for conduction of electrical impulses through the heart muscle. The direction of this electrical conduction at any point in the heart is conventionally represented by an activation vector, which is normal to an isoelectric activation front, both of which may be derived from a map of activation time. The rate of propagation of the activation front through any point in the endocardium may be represented as a velocity vector. The trajectory of points on the cardiac surface may be used to infer motion characteristics such as the contractility of the tissue. As disclosed in U.S. Pat. No. 5,738,096, issued to Ben Haim, which is incorporated herein in its entirety by reference, maps depicting such motion characteristics may be constructed when the trajectory information is sampled at a sufficient number of points in the heart.

Mapping the activation front and conduction fields aids the physician in identifying and diagnosing abnormalities, such as ventricular and atrial tachycardia and ventricular and atrial fibrillation, which result from areas of impaired electrical propagation in the heart tissue.

Localized defects in the heart's conduction of activation signals may be identified by observing phenomena such as multiple activation fronts, abnormal concentrations of activation vectors, or changes in the velocity vector or deviation of the vector from normal values. Examples of such defects include re-entrant areas, which may be associated with signal patterns known as complex fractionated electrograms. Once a defect is located by such mapping, it may be ablated (if it is functioning abnormally) or otherwise treated to restore the normal function of the heart insofar as is possible.

Electrical activity at a point in the heart is typically measured by advancing a catheter containing an electrical sensor at or near its distal tip to that point in the heart, contacting the tissue with the sensor and acquiring data at that point. One drawback with mapping a cardiac chamber using a catheter containing only a single, distal tip electrode is the long period of time required to accumulate data on a point-by-point basis over the requisite number of points required for a detailed map of the chamber as a whole. Accordingly, multiple-electrode catheters have been developed to simultaneously measure electrical activity, such as local activation times (LAT) at multiple sampled points in the heart chamber.

SUMMARY OF THE INVENTION

Typically, in order to measure conduction velocity of the electropotential at a selected point in a heart chamber, two electrodes are positioned at the point in the heart chamber at a known distance from each other, and the time difference between the occurrence of the electropotential at each electrode is measured. The speed of propagation is then simply the distance/time. However, this method requires that the line joining the two electrodes corresponds to the direction of travel of the electropotential, and this direction may not be known.

Embodiments of the invention use a catheter with multiple electrodes. The catheter may be a two dimensional catheter, such as a PentaRay™ catheter with multiple splines, or a three-dimensional catheter such as a balloon or basket catheter. The catheter has a central electrode, which may be positioned on a selected point. The spatial distribution of the electrodes surrounding the central electrode is set to correspond to a Fibonacci array, and the electrodes are then placed on splines (for the two-dimensional catheter) or a balloon/basket for the three-dimensional catheter. The inventors have noticed that electrodes distributed on splines configured as Fibonacci spirals have the property that certain triangles defined by the electrodes are approximately equilateral. Because the electrodes define approximately equilateral triangles, the value of the conduction velocity of the electropotential can be determined, and the accuracy of the determination is approximately invariant regardless of the direction of the propagation of the electropotential. Typically this is done within about 2.0 mm of the central electrode. However the neighborhood can be from 0.5 to 3.0 mm.

There is provided according to embodiments of the invention a catheter having at least one lumen extending longitudinally therethrough and a mapping assembly having a plurality of splines mounted at the distal portion of the catheter body. Each of the splines has a proximal end disposed at the distal portion of the catheter body and a distal end and configured as a Fibonacci spiral arm that diverges outwardly from the proximal end. The splines each have a support arm with shape memory, a non-conductive covering in surrounding relation to the support arm, at least one location sensor mounted at or near the distal end, a plurality of electrodes mounted in surrounding relation to the non-conductive covering, and a plurality of electrode lead wires extending within the non-conductive covering. Each electrode lead wire is attached to a corresponding one of the electrodes.

According to a further aspect of the catheter, the electrodes are disposed at distances from the proximal end of the respective splines that correspond to a Fibonacci sequence.

According to one aspect of the catheter, the splines further comprise a tip electrode mounted at or near the respective distal end thereof, electrically isolated from the support arm.

According to yet another aspect of the catheter, the mapping assembly is moveable between an expanded arrangement, in which each of the splines extends radially outward from the catheter body, and a collapsed arrangement, in which each of the splines is disposed generally along a longitudinal axis of the catheter body.

According to another aspect of the catheter, the splines are disposed on an expandable balloon, and the distal ends thereof bend in the expanded arrangement and converge at a central point.

According to still another aspect of the catheter, the splines comprise a first set of spiral arms having a left-directed curvature and a second set of spiral arms having a right-directed curvature that intersect the first set of spiral arms.

According to yet another aspect of the catheter, the distal ends of the splines converge at a central point in the expanded arrangement to define a basket.

According to a further aspect of the catheter, a tip electrode is disposed at the central point.

According to still another aspect of the catheter, the mapping assembly has eight splines.

According to an additional aspect of the catheter, the mapping assembly has 12 splines.

According to yet another aspect of the catheter, a group of electrodes of neighboring splines are disposed so as to define approximately equilateral triangles, wherein a deviation from equilaterality of the triangles does not exceed 20%.

There is further provided according to embodiments of the invention a method, which is carried out by introducing a catheter into a heart to be mapped. The catheter has at least one lumen extending longitudinally therethrough and a mapping assembly having a plurality of splines mounted at the distal portion of the catheter body. Each of the splines has a proximal end disposed at the distal portion of the catheter body and a distal end and configured as a Fibonacci spiral arm that diverges outwardly from the proximal end. The splines each have a support arm with shape memory, a non-conductive covering in surrounding relation to the support arm, at least one location sensor mounted at or near the distal end, a plurality of electrodes mounted in surrounding relation to the non-conductive covering, and a plurality of electrode lead wires extending within the non-conductive covering. Each electrode lead wire is attached to a corresponding one of the electrodes. The method is further carried out by positioning the mapping assembly so that at least one electrode from each spine is in contact with a respective location in the heart, and recording respective electrical data from the at least one electrode.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein:

FIGS. 3A and 3B, referred to collectively as FIG. 3, comprise a schematic diagram of a layout of a catheter comprising multiple splines in accordance with an embodiment of the invention;

DETAILED DESCRIPTION OF THE INVENTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

Overview

Figure 1:
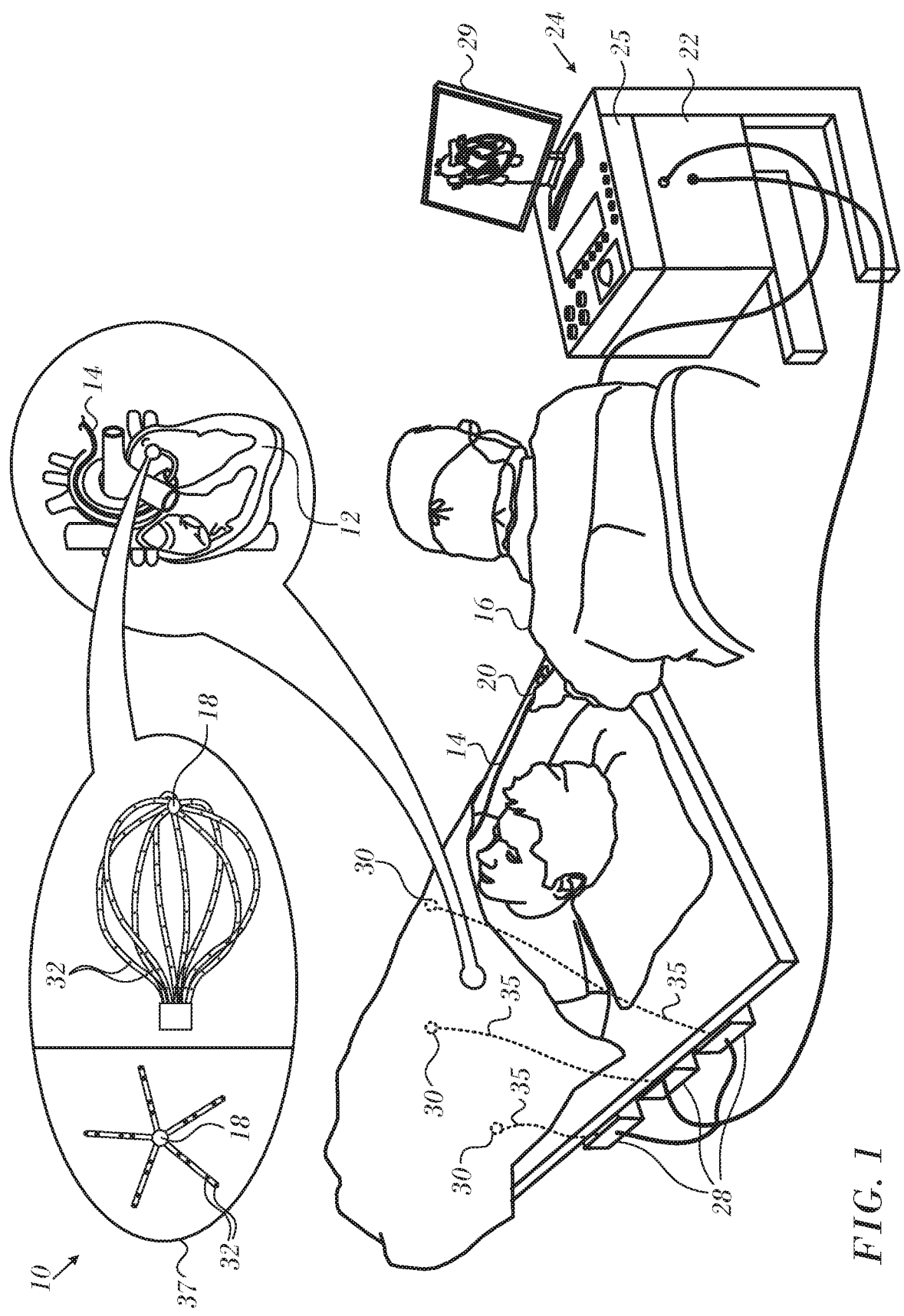
FIG. 1 is a pictorial illustration of a system for evaluating electrical activity in a heart of a living subject in accordance with an embodiment of the invention.

Turning now to the drawings, reference is initially made to FIG. 1, which is a pictorial illustration of a system 10 for performing diagnostic and therapeutic procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall, for example, at an ablation target site. Electrical activation maps may be prepared, according to the methods disclosed in U.S. Pat. Nos. 6,226,542, and 6,301,496, and in commonly assigned U.S. Pat. No. 6,892,091, whose disclosures are herein incorporated by reference.

The system 10 may comprise a general purpose or embedded computer processor, which is programmed with suitable software for carrying out the functions described hereinbelow. Thus, although portions of the system 10 shown in other drawing figures herein are shown as comprising a number of separate functional blocks, these blocks are not necessarily separate physical entities, but rather may represent, for example, different computing tasks or data objects stored in a memory that is accessible to the processor. These tasks may be carried out in software running on a single processor, or on multiple processors. The software may be provided to the processor or processors on tangible non-transitory media, such as CD-ROM or non-volatile memory. Alternatively or additionally, the system 10 may comprise a digital signal processor or hard-wired logic. One commercial product embodying elements of the system 10 is available as the CARTO® 3 System, available from Biosense Webster, Inc., 3333 Diamond Canyon Road, Diamond Bar, Calif. 91765. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically above 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to diagnose and treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a processor 22, located in a console 24. The processor 22 may fulfill several processing functions as described below.

The catheter 14 is a multi-electrode catheter, which can be a balloon or basket catheter as shown in the right portion of balloon 37, or a spline catheter as shown in the left portion. In any case there are multiple electrodes 32, which are used as sensing electrodes and have known locations on the basket or spline, and known relationships to one another. Thus, once the catheter is located in the heart, for example by constructing a current position map, the location of each of the electrodes 32 in the heart is known. One method for generation of a current position map is described in commonly assigned U.S. Pat. No. 8,478,383 to Bar-Tal et al., which is herein incorporated by reference.

Electrical signals can be conveyed to and from the heart 12 from the electrodes 32 located at or near the distal tip 18 of the catheter 14 via cable 34 to the console 24. Pacing signals and other control signals may be conveyed from the console 24 through the cable 34 and the electrodes 32 to the heart 12.

Wire connections 35 link the console 24 with body surface electrodes 30 and other components of a positioning sub-system for measuring location and orientation coordinates of the catheter 14. The processor 22, or another processor (not shown) may be an element of the positioning subsystem. The electrodes 32 and the body surface electrodes 30 may be used to measure tissue impedance at the ablation site as taught in U.S. Pat. No. 7,536,218, issued to Govari et al., which is herein incorporated by reference. A temperature sensor (not shown), typically a thermocouple or thermistor, may be mounted near the distal tip 18 of the catheter 14.

The console 24 typically contains one or more ablation power generators 25. The catheter 14 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

In one embodiment, the positioning subsystem comprises a magnetic position tracking arrangement that determines the position and orientation of the catheter 14 by generating magnetic fields in a predefined working volume and sensing these fields at the catheter, using field generating coils 28. A suitable positioning subsystem is described in U.S. Pat. No. 7,756,576, which is hereby incorporated by reference, and in the above-noted U.S. Pat. No. 7,536,218.

As noted above, the catheter 14 is coupled to the console 24, which enables the operator 16 to observe and regulate the functions of the catheter 14. Console 24 includes a processor, preferably a computer with appropriate signal processing circuits. The processor is coupled to drive a monitor 29. The signal processing circuits typically receive, amplify, filter and digitize signals from the catheter 14, including signals generated by the above-noted sensors and a plurality of location sensing electrodes (not shown) located distally in the catheter 14. The digitized signals are received and used by the console 24 and the positioning system to compute the position and orientation of the catheter 14 and to analyze the electrical signals from the electrodes as described in further detail below.

Typically, the system 10 includes other elements, which are not shown in the figures for the sake of simplicity. For example, the system 10 may include an electrocardiogram (ECG) monitor, coupled to receive signals from one or more body surface electrodes, so as to provide an ECG synchronization signal to the console 24. As mentioned above, the system 10 typically also includes a reference position sensor, either on an externally applied reference patch attached to the exterior of the subject's body, or on an internally-placed catheter, which is inserted into the heart 12 and maintained in a fixed position relative to the heart 12. The system 10 may receive image data from an external imaging modality, such as an MRI unit or the like and includes image processors that can be incorporated in or invoked by the processor 22 for generating and displaying images.

Fibonacci Sequence.

Wikipedia briefly describes Fibonacci numbers: In mathematics, the Fibonacci numbers are the numbers in the following integer sequence, called the Fibonacci sequence, and characterized by the fact that every number after the first two is the sum of the two preceding ones:

1, 1, 2, 3, 5, 8, 13, 21, 34, 55, 89, 144.

Figure 2:
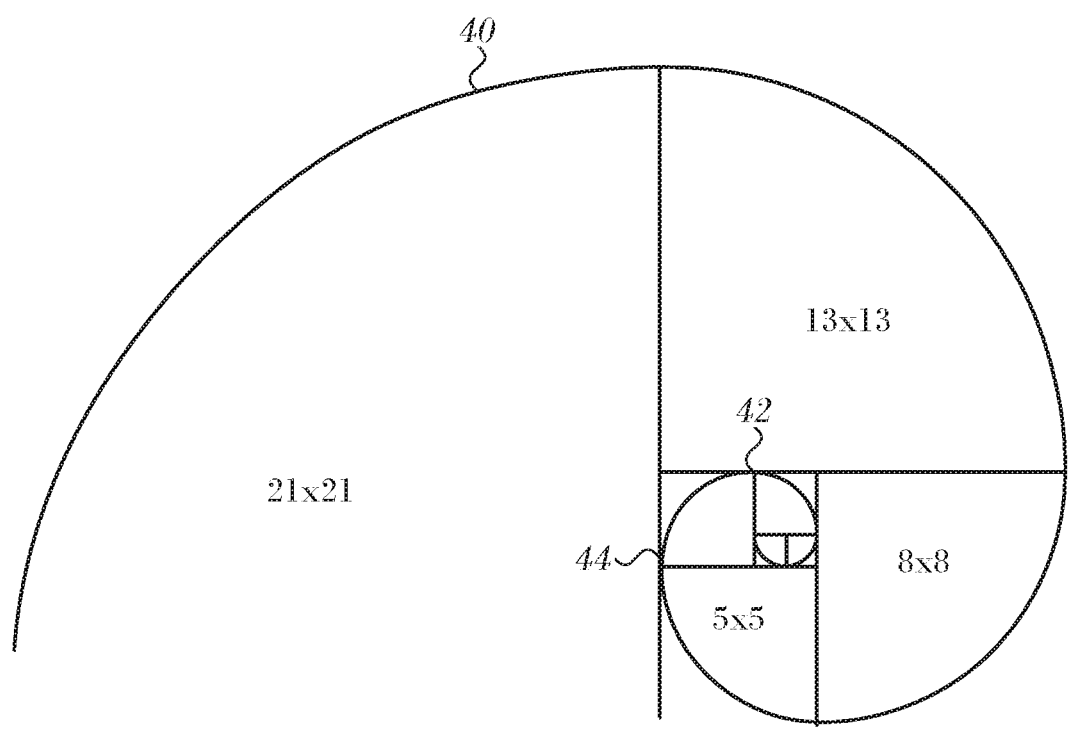
FIG. 2 is a diagram illustrating construction a Fibonacci spiral, which can be employed in an embodiment of the invention.

Reference is now made to FIG. 2, which is a diagram illustrating one well-known method of approximating a logarithmic spiral by forming a tiling with squares whose side lengths are successive Fibonacci numbers beginning at a point of origin. Spiral 40, formed of circular arcs passing through the corners of the squares, e.g., corners 42, 44 approaches a golden spiral as the spiral diverges outwardly from the origin, because the ratio of each element in the Fibonacci sequence to the preceding element converges on Phi, 1.618, known as the golden ratio, as the series progresses. For example, the series 1, 1, 2, 3, 5, 8 and 13 produce ratios of 1, 2, 1.5, 1.67, 1.6 and 1.625, respectively.

Figure 3A:
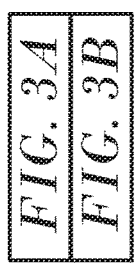
Figure 3A:
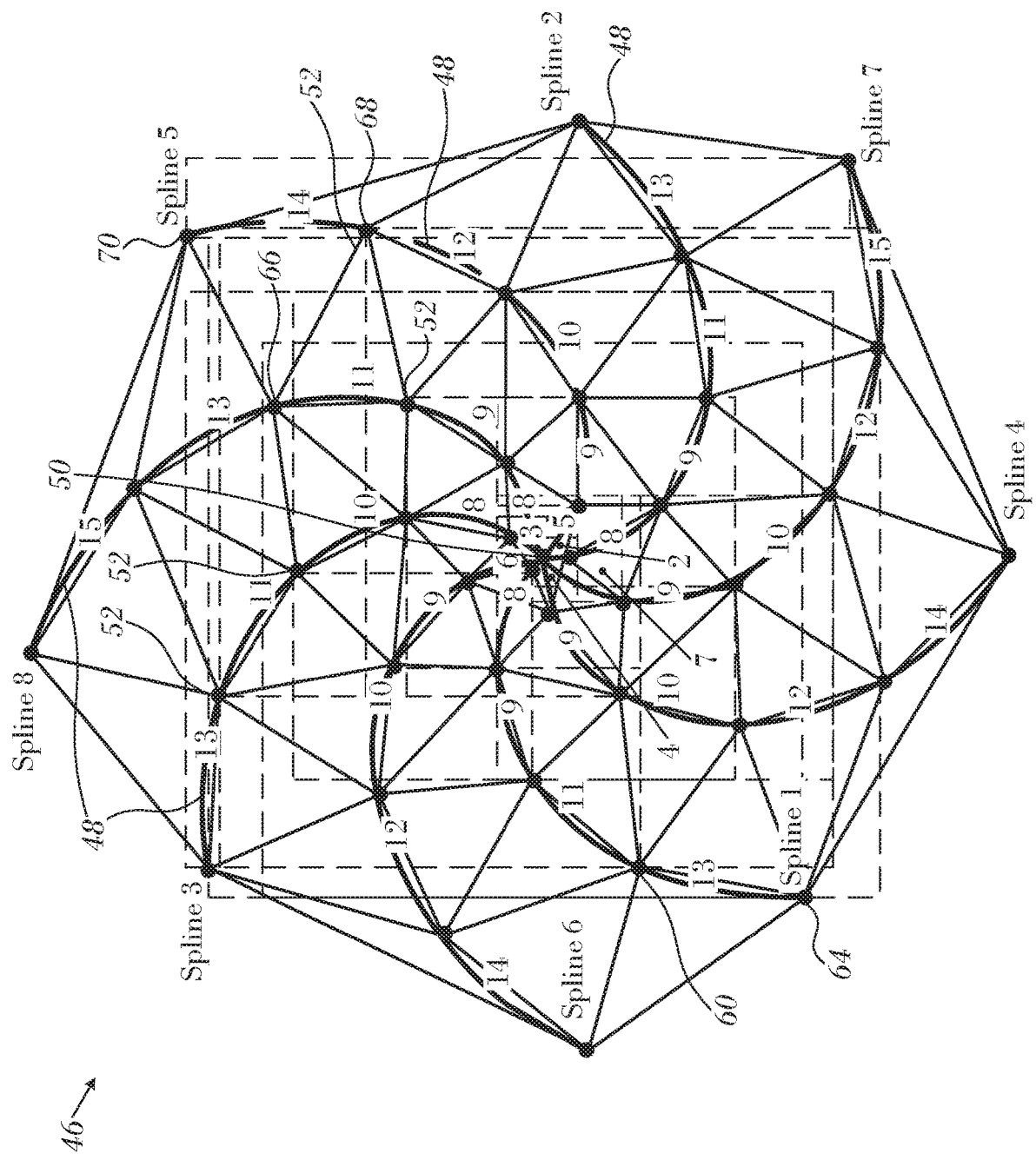

Reference is now made to FIG. 3, which is a schematic diagram of a layout 46 of a catheter comprising multiple splines 48 in accordance with an embodiment of the invention. In embodiments of a 3-dimensional balloon catheter, the splines may be constructed on the surface as Fibonacci spiral forms, as described with respect to FIG. 2, the splines 48 all converging at a central point 50 and preferably equally distributed about the circumference of the balloon. Electrodes 52 are disposed along the splines 48. The respective distances between electrodes 52 from along each spline increase according to the Fibonacci sequence. In this embodiment the spacing of electrodes 52 is given in table 54. Eight sets of coefficients of spline equation 56 are given in table 58, applicable to the eight splines shown in the layout 46. In the layout 46 many approximately equilateral triangles are defined. For example, electrodes at points 60, 62, 64 define such a triangle, as do electrodes at points 66, 68, 70. In practice a deviation from equilaterality of 20% can be tolerated.

Figure 4:
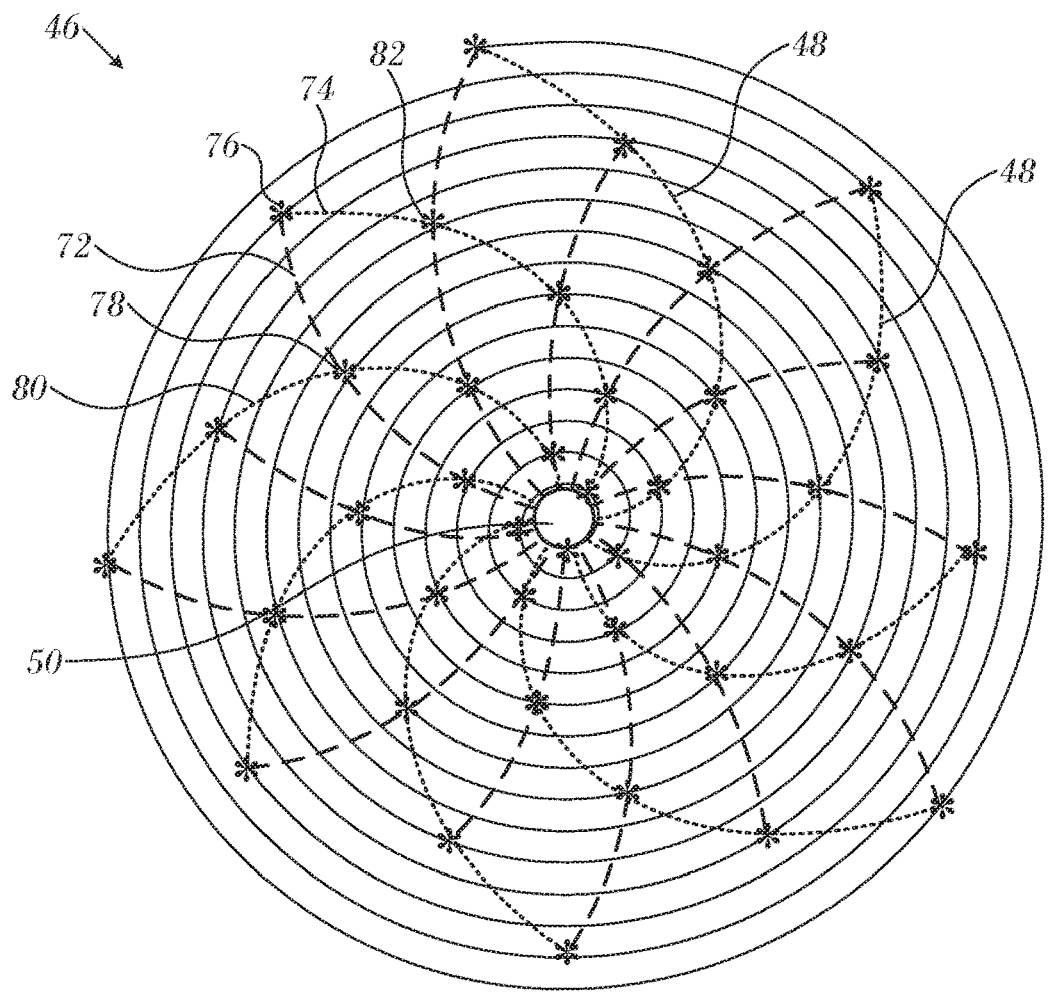
FIG. 4 is a diagram illustrating a layout of Fibonacci spirals in accordance with an embodiment of the invention.

Reference is now made to FIG. 4, which is a diagram illustrating a layout with two intersecting sets of Fibonacci spirals having opposite curvatures in accordance with an embodiment of the invention, one set having a left-directed curvature and the other set having a right-directed curvature. The terms "left-directed" and "right-directed" are used arbitrarily herein to distinguish the curvatures of the spirals. For example spirals 72, 74 are in different sets. Electrodes are disposed at the intersection of the sets, such as electrode 76, which is at an intersection of the spiral 72 and its neighboring spiral 74. Similarly, electrode 78 is located at the intersection of spirals 72, 80. Electrodes 78, 76, 82, all on intersections of neighboring spirals define a triangle, which is approximately equilateral. The two sets of spirals can be constructed using the equation 56 (FIG. 3) with an appropriate change in direction The opposing splines form a weave, which when incorporated into a balloon assembly of a catheter advantageously tends to stabilize the balloon surface. Such balloon assemblies can be constructed according to the teachings of commonly assigned U.S. Patent Application Publication No. 2016/0324571, entitled Spring Loaded Balloon, which is herein incorporated by reference. Construction.

Figure 5:
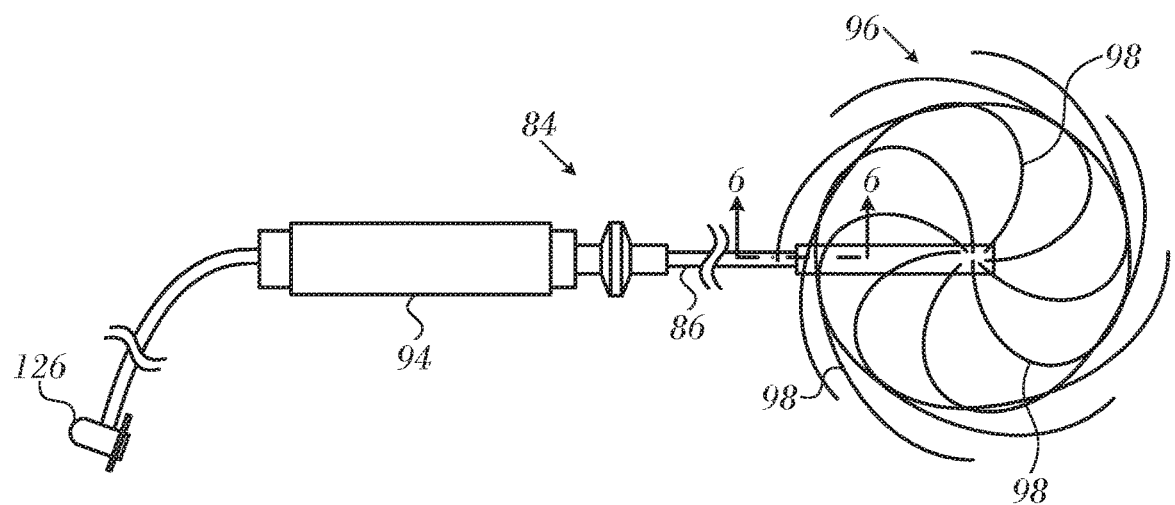
FIG. 5 is a schematic side elevation of a catheter in accordance with an embodiment of the invention.

Reference is now made to FIG. 5, which is a schematic side elevation of a catheter 84 in accordance with an embodiment of the invention. Catheter body 86 comprises an elongated tubular construction having a single, axial or central lumen 88, but can optionally have multiple lumens along all or part of its length if desired. The catheter body 86 is flexible, i.e., bendable, but substantially non-compressible along its length. The catheter body 86 can be of any suitable construction and made of any suitable material.

Figure 6:
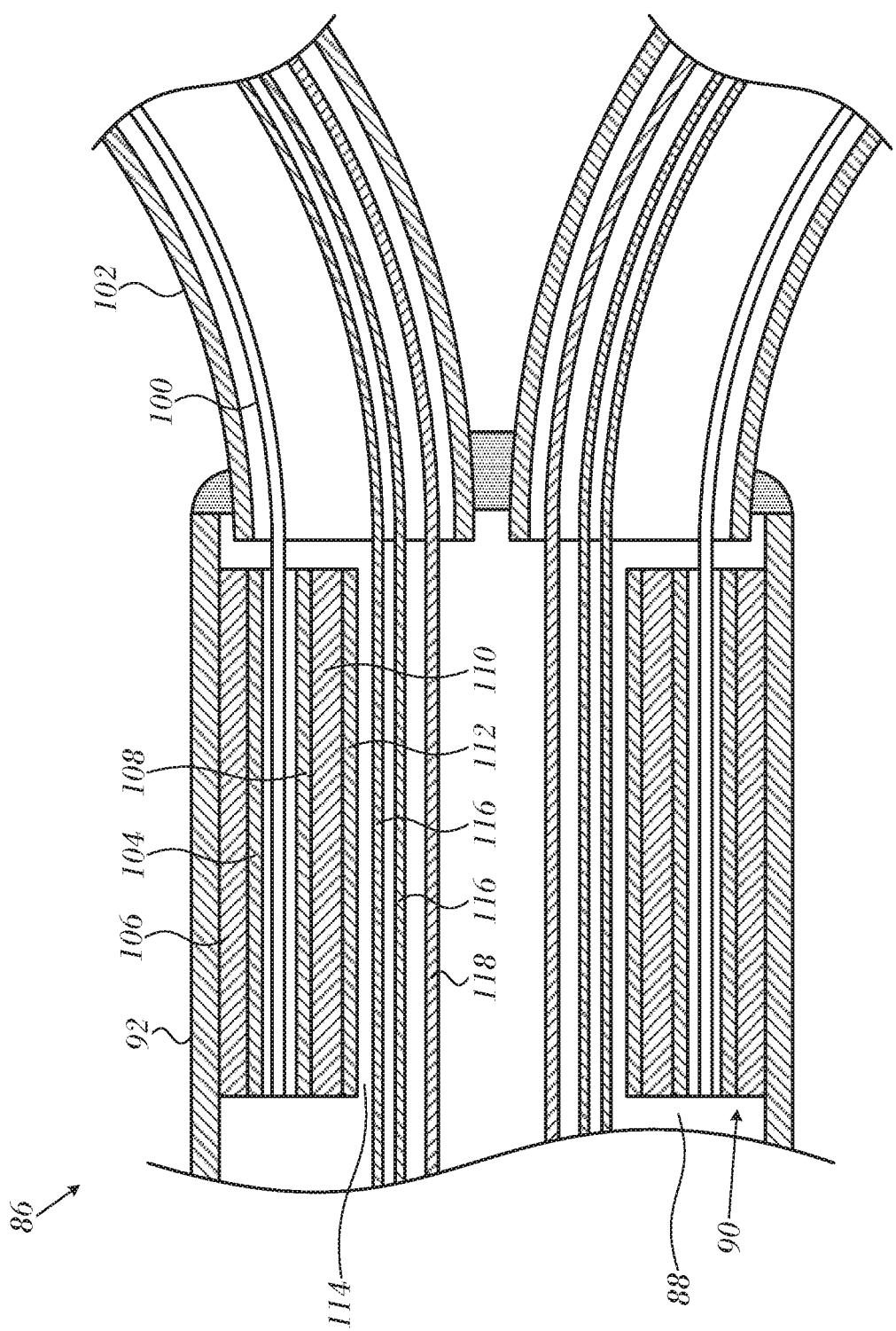
FIG. 6, which is a sectional schematic view of a portion of the catheter of FIG. 5 taken through line 6-6 in accordance with an embodiment of the invention.

Reference is made to FIG. 6, which is a sectional schematic view of a portion of the catheter of FIG. 5, taken through line 6-6 in accordance with an embodiment of the invention. Mounted in the distal end of the lumen 88 of the catheter body 86 is a spine mounting assembly 90.

One construction of the catheter body 86 comprises an outer wall 92 made of polyurethane or Pebax® (polyether block amide). The outer wall 92 comprises an imbedded braided mesh of stainless steel or the like, as is generally known in the art, to increase torsional stiffness of the catheter body 86 so that, when a control handle 94 is rotated, the distal end of the catheter body 86 rotates in a corresponding manner.

The length of the catheter body 86 is not critical, but preferably ranges from about 190 cm to about 120 cm, and more preferably is about 110 cm. The outer diameter of the catheter body 86 is also not critical, but is preferably no more than about 8 french, more preferably about 7 french. Likewise, the thickness of the outer wall 92 is not critical, but is preferably thin enough so that the central lumen 88 can accommodate puller wires, lead wires, sensor cables and any other wires, cables or tubes. If desired, the inner surface of the outer wall 92 is lined with a stiffening tube (not shown) to provide improved torsional stability. An example of a catheter body construction suitable for use in connection with the present invention is described and depicted in U.S. Pat. No. 6,064,905, the entire disclosure of which is incorporated herein by reference.

In the depicted embodiment, a mapping assembly 96 comprises eight splines 98, which are configured as Fibonacci spirals, as described above. Each of the splines 98 has a proximal end attached at the distal end of the catheter body 86 and a free distal end, i.e., the distal end is not attached to any of the other splines, to the catheter body, or to any other structure that confines movement of the distal end. Each of the splines 98 contains a support arm 100 comprising a metal or plastic material that has shape memory, such that the support arm 100 forms an initial shape when no external forces are applied, forms a deflected shape when an external force is applied, and returns to its initial shape when the external force is released. In a preferred embodiment, the support arm 100 comprises a superelastic material, for example a nickel-titanium alloy, such as Nitinol. Each of the splines 98 also comprises a non-conductive covering 102 in surrounding relation to the support arm 100. In a preferred embodiment, the non-conductive covering 102 comprises a biocompatible plastic tubing, such as a polyurethane or polyimide tubing.

A first non-conducting tube 104 is disposed between an outer mounting ring 106 and the support arm 100, and a second non-conducting tube 108 is disposed between the support arm 100 and a mounting structure 110. The non-conducting tubes 104, 108, which may be polyimide tubes, ensure that each support arm 100 remains electrically isolated. In addition, a mounting ring inner tube 112 is secured within the mounting structure 110. The mounting ring inner tube 112 preferably comprises a non-conducting material such as polyimide. The mounting ring inner tube 112 defines a mounting ring lumen 114 through which electrode lead wires 116 and sensor cables 118 extend.

As will be recognized by one skilled in the art, the number of splines 98 can vary as desired depending on the particular application, so that the catheter has at least two splines, preferably at least three splines, more preferably at least eight splines and as many as 12 or more splines. As described in more detail below, the splines 98 are moveable between an expanded arrangement, wherein, for example, each spline spirals outwardly from the catheter body 86, or the splines 98 may be arranged in a collapsed arrangement, wherein, for example, each spline is disposed generally along a longitudinal axis of the catheter body 86 so that the splines are capable of fitting within a lumen of a guiding sheath.

Figure 7:
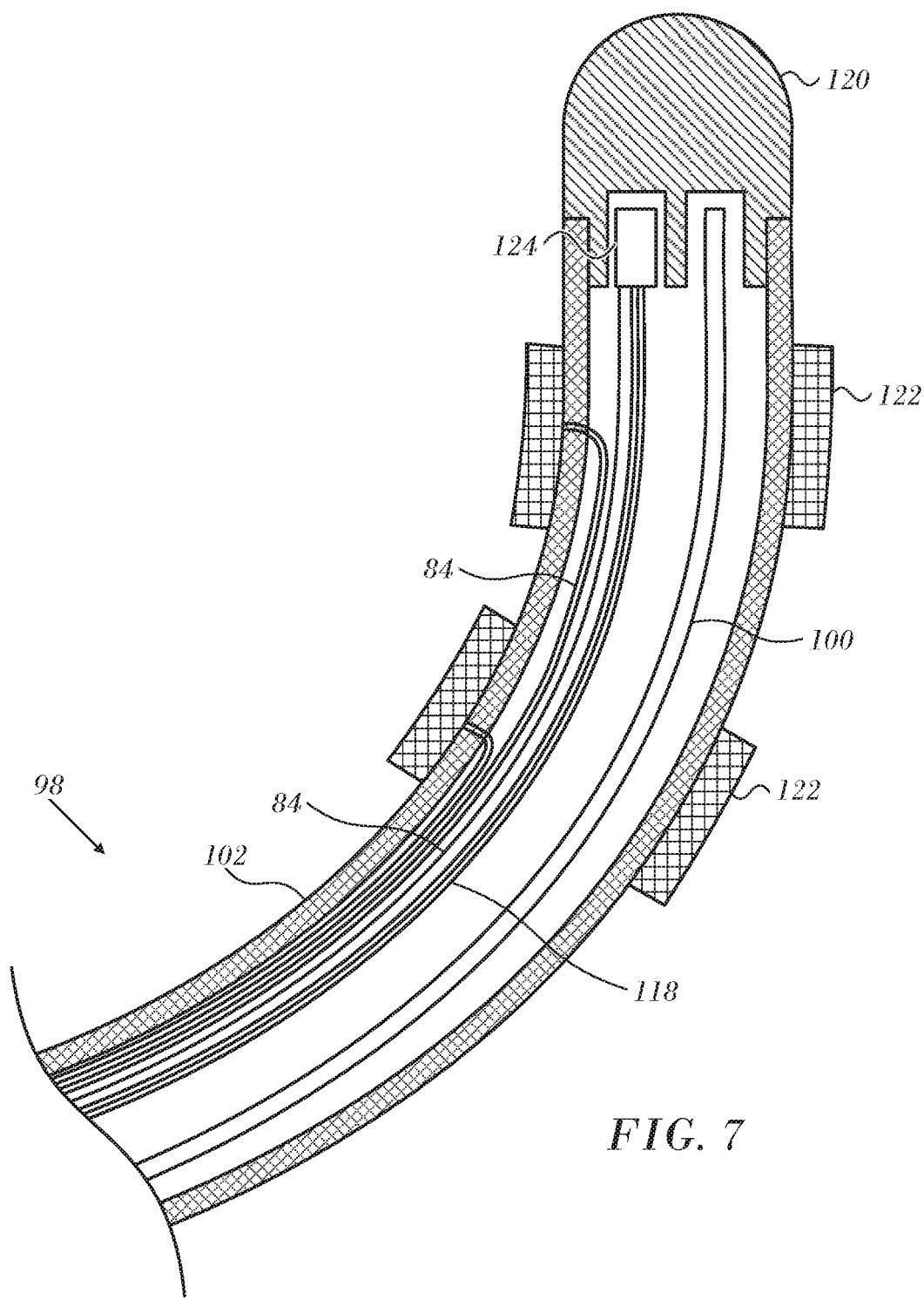
FIG. 7 is a longitudinal sectional view of one of the splines in the catheter shown in FIG. 5 in accordance with an embodiment of the invention.

Reference is made to FIG. 7, which is a longitudinal sectional view of one of the splines 98 (FIG. 5), in accordance with an embodiment of the invention. Each of the splines 98 carries at least one electrode mounted along its length, disposed as described above. In the depicted embodiment, a tip electrode 120 may be mounted on a distal end of each non-conductive covering 102 and at least one ring electrode 122 is mounted on each non-conductive covering 102, preferably on the distal end of the non-conductive covering 102. In a bipolar arrangement, the ring electrode 122 is used as a reference electrode. The distance between the tip electrode and ring electrode preferably ranges from about 0.5 mm to about 2 mm. In an alternative bipolar arrangement (not shown), the tip electrode 120 is eliminated and at least two ring electrodes 122 are mounted on each non-conductive covering 102, preferably on the distal end of the non-conductive covering 102. Another alternative embodiment (not shown), is a unipolar arrangement, in which the tip electrode 120 is mounted on the distal end of each non-conductive covering 102, with one or more reference ring electrodes mounted on the distal end of the catheter body 86, or one or more reference electrodes attached outside the body of the patient (e.g., in the form of a patch). In an alternative unipolar arrangement, a ring electrode 122 mounted on each non-conductive covering 102, preferably on the distal end of the non-conductive covering 102, is used instead of tip electrode 120.

Each of the splines 98 may also include at least one location sensor 124. The location sensor 124 is mounted near the distal end of each spine. In the depicted embodiment, where each spline 98 comprises tip electrode 120. The location sensor 124 is mounted such that the distal end of the location sensor 124 is secured within its corresponding tip electrode 120, while the proximate end of the location sensor 124 extends into the distal end of the non-conductive covering 102. Each location sensor 124 is used to determine the coordinates of its corresponding tip electrode 120 at each instant when the tip electrode 120 is being used to collect an electrical mapping data point. As a result, both electrical and locational data can be obtained for each data point that is mapped. If the spline 98 carries at least one ring electrode 28 but does not include the tip electrode 120, the location sensor 124 is mounted near the distal end of the non-conductive covering 102, preferably as close to the distal end of the spline 98 as possible or in a plane concentric with the ring electrode 122.

Each location sensor 124 is connected to a corresponding sensor cable 118. Each sensor cable 118 extends through the non-conductive covering 102, catheter body 86 and control handle 94 and out the proximal end of the control handle 94.

Each tip electrode 120 has an exposed length preferably ranging from about 0.5 mm to about 4 mm, more preferably from about 0.5 mm to about 2 mm, still more preferably about 1 mm. Each ring electrode 122 has a length preferably up to about 2 mm, more preferably from about 0.5 mm to about 1 mm.

Each tip electrode 120 and each ring electrode 122 is electrically connected to an electrode lead wire 116, which in turn is electrically connected to a connector 126 (FIG. 5). The connector 126 is connected to an appropriate mapping or monitoring system (not shown). Each electrode lead wire 116 extends from the connector 126, through the control handle 94, through the central lumen 88 in the catheter body 86, and into the non-conductive covering 102 of the splines 98 where it is attached to its corresponding tip electrode 120 or ring electrode 122. Each lead wire 116, which includes a non-conductive coating over almost all of its length, is attached to its corresponding tip electrode 120 or ring electrode 122 by any suitable method.

Additional details of the construction of the catheter are found in commonly assigned U.S. Patent Application Publication No. 20060276703, which is herein incorporated by reference.

Figure 8:
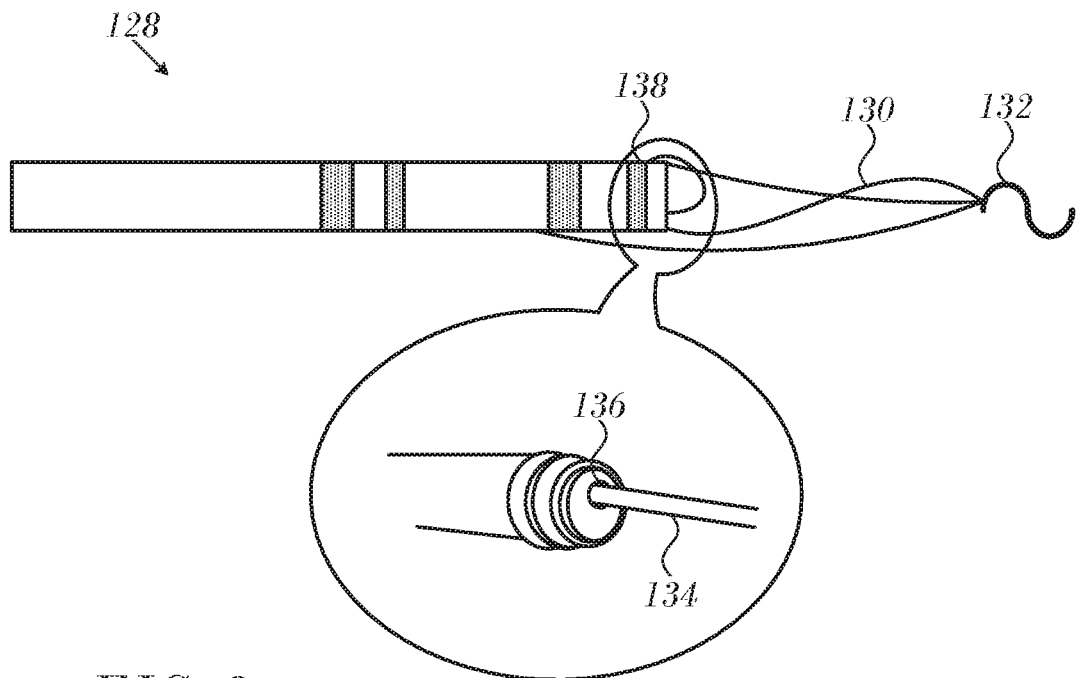
FIG. 8 is a schematic diagram of a partially unfolded catheter in accordance with an embodiment of the invention.

Reference is now made to FIG. 8, which is a schematic diagram of a partially unfolded catheter 128 in accordance with an embodiment of the invention. Spiral assembly 130 may be provided with a distal locking element, such as a hook 132. The assembly 130 is attached to a rotator shaft 134, which is inserted through a lumen 136 of the catheter 128. As the assembly 130 extends beyond distal end 138 of the catheter 128 it eventually encounters a wall of the atrium, and is held in place against the wall by the hook 132. Deployment of the assembly 130 is then completed by retracting and concurrently turning the rotator shaft 134, causing the assembly 130 to assume an expanded spiral configuration as shown in FIG. 5.

Velocity Vector Calculations.

Figure 9:
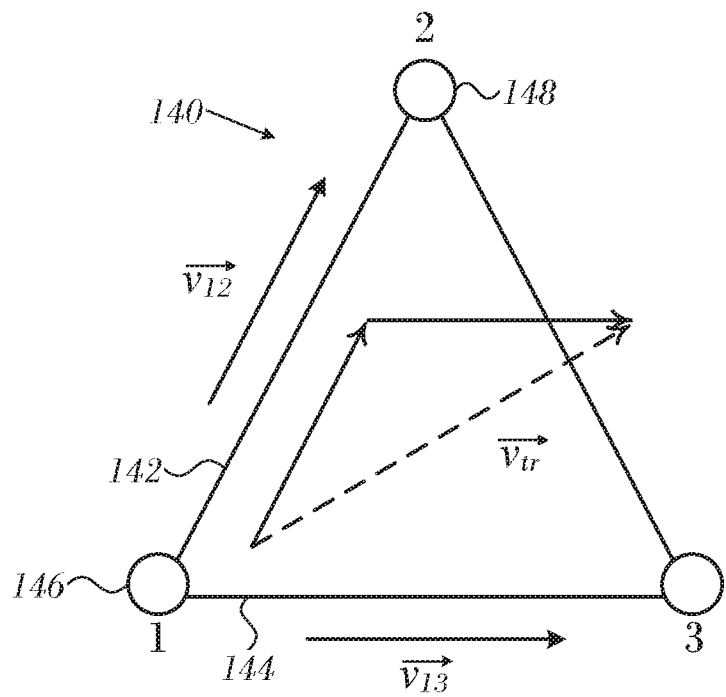
FIG. 9 is a diagram illustrating the calculation of velocity vectors for an electrical wave on a triangular mesh in accordance with an embodiment of the invention.

The approximately equilateral triangles defined by the electrodes in FIG. 3 can be regarded as a triangular mesh. Reference is now made to FIG. 9, which is a diagram illustrating the calculation of velocity vectors for an electrical wave on a triangular mesh in accordance with an embodiment of the invention. Triangle 140 has edges, including edges 142, 144. A velocity vector exists at each edge. For example, the velocity vector $\vec{v}_{12}$ for edge 142 is given by $$\vec{v}_{12} = \frac{d_{12}}{(lat_2 - lat_1)} \quad \text{Eq. (1)}$$

where $d_{12}$ is the distance between vertices 146, 148 of triangle 140, and $lat_1$ and $lat_2$ are the activation times at vertices 146, 148. The velocity vector for edge 144 is calculated in like manner.

The velocity $\vec{v}_{tr}$ through triangle 140 is the sum of velocities along edges 142, 144:

$$\vec{v}_{tr} = \vec{v}_{12} + \vec{v}_{13} \quad \text{Eq. (2)}$$

Because the electrodes define approximately equilateral triangles, the accuracy of the determination of the velocity vector is approximately invariant regardless of the direction of the electrical propagation. Further details on evaluating propagation through the heart, which can be advantageously accomplished using the principles of the present invention may be found in commonly assigned application Ser. No. 15/086,220, entitled Mapping of Atrial Fibrillation, which is herein incorporated by reference.

Alternate Embodiment

In this embodiment 3-dimensional splines formed as Fibonacci spirals are realized in a balloon catheter. Except for the spiral arrangement of the splines, a catheter of this sort can be constructed and introduced conventionally, as described, for example in commonly assigned U.S. Patent Application Publication Nos. 20160175041 entitled Balloon for Ablation around Pulmonary Veins, 20160324571 entitled Spring-Loaded Balloon, and U.S. Pat. No. 9,352,134 entitled Segmented Balloon Catheter, which are all herein incorporated by reference.

Figure 10:
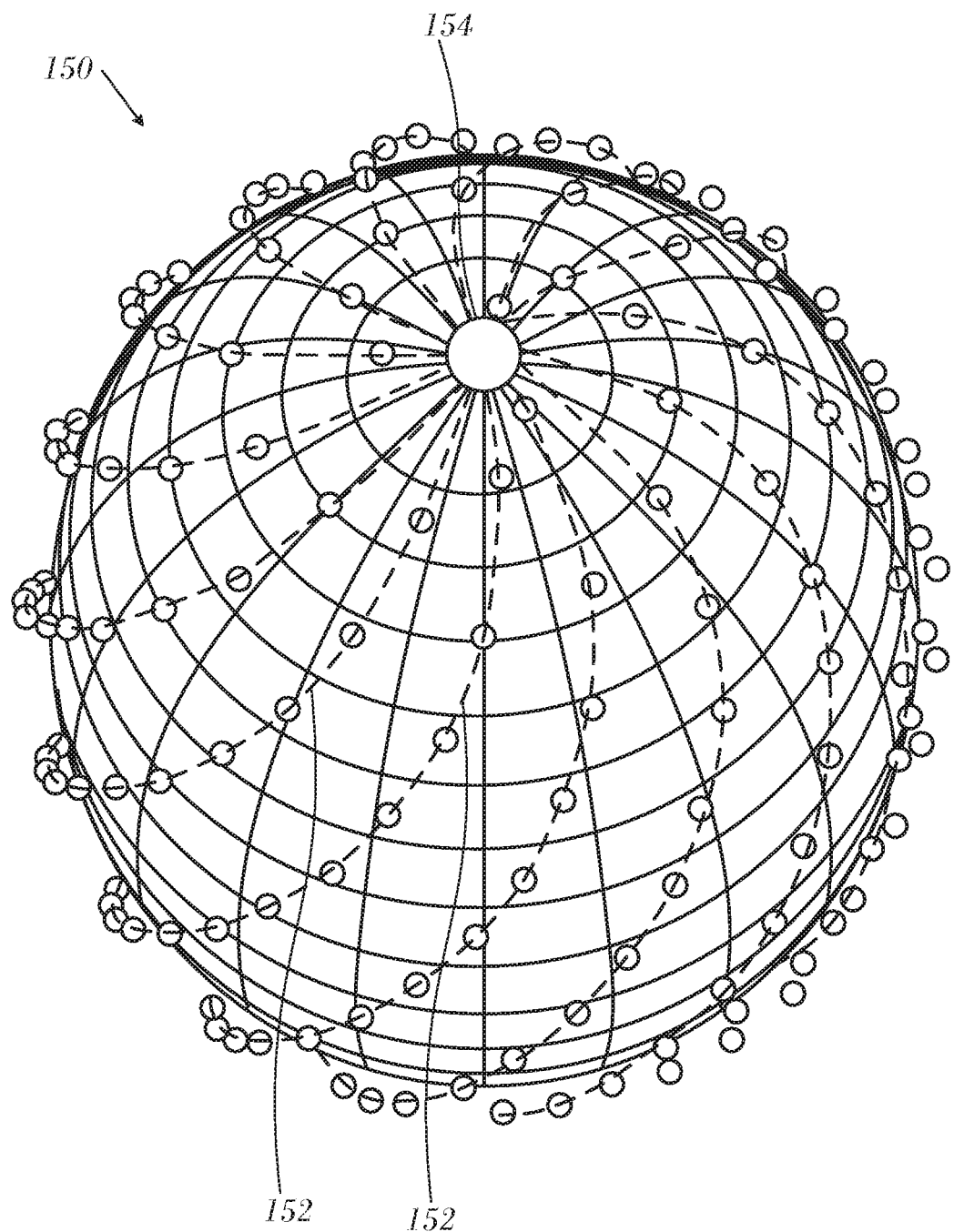
FIG. 10 is a schematic diagram of a spline assembly in accordance with an embodiment of the invention.

Reference is now made to FIG. 10, which is a schematic diagram of a 3-dimensional spline assembly 150, in accordance with an embodiment of the invention. Splines 152, configured as Fibonacci spirals as described above, but now stretched to form a 3-dimensional surface, extend from a central location 154, which may comprise a central electrode, along the surface of the assembly 150. The splines 152, when distorted in this manner, form a sphere or an ellipsoid with a major diameter generally aligned with the axial dimension of the assembly 150. The 2-dimensional spline arrangement shown in FIG. 4 may be deformed to form such a 3-dimensional structure.

In alternate embodiments the splines 152 may be adhered to the exterior surface, the interior surface, or be embedded within the substance of a balloon. Alternatively the splines may form a basket catheter as is known in the art. Electrodes (not shown) are distributed on the splines at distances from the central location 154 corresponding to the Fibonacci sequence.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A catheter comprising:
an elongated catheter body having a distal portion and at least one lumen extending longitudinally therethrough; and
a mapping assembly mounted at the distal portion of the catheter body and comprising a plurality of splines, each of the splines having a proximal end disposed at the distal portion of the catheter body and a distal end and configured as a Fibonacci spiral arm that follows a portion of a Fibonacci sequence so as to diverge outwardly from the proximal end, wherein each of the splines comprises:
a support arm having shape memory;
a non-conductive covering in surrounding relation to the support arm; at least one location sensor mounted at or near the distal end;
a plurality of electrodes mounted in surrounding relation to the non-conductive covering; and
a plurality of electrode lead wires extending within the non-conductive covering, each electrode lead wire being attached to a corresponding one of the electrodes.

2. The catheter according to claim 1, wherein the electrodes are disposed at distances from the proximal end of the respective splines that correspond to a Fibonacci sequence.

3. The catheter according to claim 1, wherein the splines further comprise a tip electrode mounted at or near the respective distal end thereof and electrically isolated from the support arm.

4. The catheter according to claim 1, wherein the mapping assembly is moveable between an expanded arrangement, in which each of the splines extends radially outward from the catheter body, and a collapsed arrangement, in which each of the splines are disposed generally along a longitudinal axis of the catheter body.

5. The catheter according to claim 4, wherein the splines are disposed on an expandable balloon, and the distal ends thereof bend in the expanded arrangement and converge at a central point.

6. The catheter according to claim 5, wherein the splines comprise a first set of spiral arms having a left-directed curvature and a second set of spiral arms having a right-directed curvature that intersect with a number of the first set of spiral arms.

7. The catheter according to claim 5, wherein a tip electrode is disposed at the central point.

8. The catheter according to claim 4, wherein the distal ends of the splines converge at a central point in the expanded arrangement to define a basket.

9. The catheter according to claim 8, wherein a tip electrode is disposed at the central point.

10. The catheter according to claim 1, wherein the mapping assembly comprises eight splines.

11. The catheter according to claim 1, wherein the mapping assembly comprises 12 splines.

12. The catheter according to claim 1, wherein a group of electrodes of the plurality of electrodes from neighboring ones of the splines are disposed so as to define approximately equilateral triangles.

13. A method comprising the steps of:
introducing a catheter into a heart to be mapped, wherein the catheter comprises:
an elongated catheter body having a distal portion and at least one lumen extending longitudinally therethrough; and
a mapping assembly mounted at the distal portion of the catheter body and comprising a plurality of splines, each of the splines having a proximal end disposed at the distal portion of the catheter body and a distal end and configured as a Fibonacci spiral arm that follows a portion of a Fibonacci sequence so as to diverge outwardly from the proximal end, wherein each of the splines comprises:
a support arm having shape memory;
a non-conductive covering in surrounding relation to the support arm; at least one location sensor mounted at or near the distal end;
a plurality of electrodes mounted in surrounding relation to the non-conductive covering; and
a plurality of electrode lead wires extending within the non-conductive covering, each electrode lead wire being attached to a corresponding one of the electrodes, the method further comprising:
positioning the mapping assembly so that at least one electrode from each spine is in contact with a respective location in the heart; and
recording respective electrical data from the at least one electrode of each spline.

14. The method according to claim 13, further comprising disposing a group of electrodes of the plurality of electrodes from neighboring ones of the splines so as to define approximately equilateral triangles, further comprising determining velocity vectors of electrical propagation from the recorded electrical data of the group of electrodes.

15. The method according to claim 13, further comprising disposing the electrodes at distances from the proximal end of the respective splines that correspond to a Fibonacci sequence.

16. The method according to claim 13, further comprising mounting a tip electrode at or near the respective distal end of the splines and electrically isolating the tip electrode from the support arm.

17. The method according to claim 13, further comprising alternating the mapping assembly between an expanded arrangement, in which each of the splines extends radially outward from the catheter body, and a collapsed arrangement, in which each of the splines is disposed generally along a longitudinal axis of the catheter body.

18. The method according to claim 17, further comprising disposing the splines as a first set of spiral arms having a left-directed curvature and a second set of spiral arms having a right-directed curvature that intersect with a number of the first set of spiral arms.

19. The method according to claim 17, further comprising disposing the splines on an expandable balloon, and converging the distal ends thereof at a central point in the expanded arrangement.

20. The method according to claim 19, further comprising disposing a tip electrode at the central point.

21. The method according to claim 17, further comprising converging the distal ends at a central point in the expanded arrangement to define a basket.

22. The method according to claim 21, wherein a tip electrode is disposed at the central point.

23. The method according to claim 13, wherein the mapping assembly comprises eight splines.

24. The method according to claim 13, wherein the mapping assembly comprises 12 splines.

* * * * *